(12) United States Patent
Olayo Gonzalez et al.

(10) Patent No.: US 8,563,626 B2
(45) Date of Patent: Oct. 22, 2013

(54) USE OF PLASMA-SYNTHESISED PYRROLE-DERIVED POLYMERS FOR THE NEUROPROTECTION AND RECONNECTION OF THE CENTRAL NERVOUS SYSTEM

(75) Inventors: Roberto Olayo Gonzalez, México (MX); Juan Morales Corona, México (MX); Rodrigo Lozano Mondragon, México (MX); Ana Laura Alvarez Mejia, México (MX); Juan Carlos Axayacatl Morales Guadarrama, México (MX); Luis Camilo Rios Castañeda, México (MX); Maria de los Angeles Araceli Diaz Ruiz, México (MX); Guillermo Jesús Cruz Cruz, México (MX); María Guadalupe Olayo González, México (MX); Hermelinda Salgado Ceballos, México (MX)

(73) Assignees: Universidad Autonoma Metropolitana, Mexico City (MX); Instituto Nacional de Neurologia Y Neurocirugia Manuel Velasco Suarez, Mexico City (MX); Instituto Mexicano del Seguro Social, Mexico City (MX); Instituto Nacional de Investigaciones Nucleares, Mexico City (MX)

(*) Notice: Subject to any disclaimer, the term of this patent is extended or adjusted under 35 U.S.C. 154(b) by 0 days.

(21) Appl. No.: 12/602,613

(22) PCT Filed: Jun. 1, 2007

(86) PCT No.: PCT/MX2007/000067
§ 371 (c)(1),
(2), (4) Date: Jun. 1, 2010

(87) PCT Pub. No.: WO2008/147166
PCT Pub. Date: Dec. 4, 2008

(65) Prior Publication Data
US 2010/0234488 A1    Sep. 16, 2010

(51) Int. Cl.
*A61F 2/02*    (2006.01)
(52) U.S. Cl.
USPC .......................................... 523/113; 528/423

(58) Field of Classification Search
USPC .......................................... 523/113; 528/423
See application file for complete search history.

(56) References Cited

U.S. PATENT DOCUMENTS

| 6,095,148 A | 8/2000 | Shastri |
| 2003/0066987 A1 | 4/2003 | Schmidt |
| 2003/0166831 A1 | 9/2003 | Shastri |

OTHER PUBLICATIONS

Cao, et al., "Preparation of Polypyrrole Film by Remote Plasma Polymerization", *Chinese J. Synthetic Chemistry*, 4(3):200 (1996) doi:cnki:ISSU:10051511.0.1996-03-002 (translation).
Lee, et al., "Carboxylic Acid-Functionalized Conductive Polypyrrole as a Bioactive Platform for Cell Adhesion", *Biomacromolecules*, vol. 7, pp. 1692-1695, 2006.
Lee, et al., "Carboxy-Endcapped Conductive Polypyrrole: Biomimetic Conducting Polymer for Cell Scaffolds and Electrodes", *Langmuir*, vol. 22, 9816-9819, 2006.
Lee, et al., "Neuroactive conducting scaffolds: nerve growth factor conjugation on active ester-functionalized polypyrrole", *J. Royal Soc. Interface*, vol. 6, pp. 801-810, 2009.
Cruz, G.J., et al., Films Obtained by Plasma Polymerization of Pyrrole; The Solid Films., vol. 342, issues 1-2, Mar. 26, 1999, pp. 119-126.

*Primary Examiner* — Kriellion Sanders
(74) *Attorney, Agent, or Firm* — Browdy and Neimark, PLLC

(57) ABSTRACT

The purpose of the present invention is to demonstrate that semiconducting and non-biodegradable implants made with polypyrrole and polyethylenglycol copolymers and iodine-doped and plasma-synthesized pyrrole polymers, have a neuroprotector effect and induce the reconnection of the spinal cord after an injury; this effect was proved in a model involving a complete section of the spinal cord in rats; the results o the functional evaluation demonstrated 5 times greater recovery in animals implanted with the polypyrrole-polyethylenglycol copolymer compared with the control group which only underwent a complete section of the spinal cord; in addition, the functional recovery of the group with iodine-doped polypyrrole was ten times greater compared to the control group; in the histological study various inflammatory and immune cells were identified at the injury site in the three experimental groups with and without implants and the integration of the polymers in the nervous tissue of the spinal cord was also observed; finally, no respiratory, renal or skin infections, adverse effects or rejection of the biomaterials were found in any of the animals.

3 Claims, 7 Drawing Sheets

USE OF PLASMA-SYNTHESISED PYRROLE-DERIVED POLYMERS FOR THE NEUROPROTECTION AND RECONNECTION OF THE CENTRAL NERVOUS SYSTEM

FIELD OF THE INVENTION

The present invention proposes the use of plasma-synthesised pyrrole-derived polymers, and non-biodegradables, for the manufacture of implants that promote neuroprotection and reconnection of spinal cord after an injury.

BACKGROUND OF THE INVENTION

The traumatic spinal cord injury (SCI) is a public health problem associated with high mortality (Dryden D M, Saunders L D, Rowe B H, May L A, Yiannakoulias N, Svenson L W, Schopflocher D P, Voaklander D C. The epidemiology of traumatic spinal cord injury in Alberta, Canada. Can. J. Neurol. Sci. 2003; 30: 113-121) and severe consequences leading to disability and long and expensive rehabilitation treatments.

Besides having a high social and economic impact, it has been reported that, in the United States, Canada, Australia, Italy and Mexico the new annual cases of SCI are in a range of 18 to 55 per million people (Woodruff B A, Baron R C. A description of nonfatal spinal cord injury using a hospital-based registry. Am. J. Prev. Med. 1994; 10: 10-14, Dryden D M, Saunders L D, Rowe B H, May L A, Yiannakoulias N, Svenson L W, Schopflocher D P, Voaklander D C. The epidemiology of traumatic spinal cord injury in Alberta, Canada. Can. J. Neurol. Sci. 2003; 30: 113-121, O'-Connor P. Incidence and patterns of spinal cord injury in Australia. Accid. Anal. Prey. 2002; 34: 405-415, Pagliacci M C, Celani M G, Zampolini M, Spizzichino L, Franceschini M, Baratta S, Finali G, Gatta G, Perdon L; Gruppo Italiano Studio Epidemiologico Mielolesioni. An Italian survey of traumatic spinal cord injury. The Gruppo Italiano Studio Epidemiologico Mielolesioni study. Arch Phys Med Rehabil. 2003; 84: 1266-1275, Pardini M C. La epidemiología de la lesión medular traumática en el Distrito Federal. PhD thesis of the Secretaría de Salubridad y Asistencia 1998).

Victims suffering from SCI now have relief and rehabilitation programs designed to stop the long-term physical deterioration (Houle J D, Tessler A. Repair of chronic spinal cord injury. Exp Neurol. 2003; 182: 247-260). However, these individuals are waiting for a treatment that can restore their autonomic functions, decreasing neuropathic pain and recover their walking ability. Because of the importance of this disease, several institutions world wide have been formed who spend annually several hundred million dollars to support the research on this subject, however, until today there are no effective treatments (Houle J D, Tessler A. Repair of chronic spinal cord injury. Exp Neurol. 2003; 182: 247-260).

The pathophysiological events of the damage start with a process of self-destruction of the nervous tissue, abortive regeneration and healing around the site of injury (Aldskogius H, Kozlova E N. Strategies for repair of the deafferented spinal cord. Brain Res Brain Res Rev. 2002; 40: 301-308). During acute stage, an ischemic process is observed, due to damage to blood microcirculation that generates an energy failure which in turn translates into a loss of ionic regulation and edema caused by the mobilization of monovalent cations such as K+ and Na+ and divalent cations such as $Ca^{2+}$, leading to spinal shock (Hulsebosch C E. Recent advances in patophysiology and treatment of spinal cord injury. Adv. Physiol. Educ. 2003; 26: 238-255).

The result of all these processes is a highly unfavorable environment for carrying out the healing processes of damaged tissue both in the injury site and in its periphery (Beattie M S, Farooqui A A, Bresnahan J C. Review of current evidence for apoptosis after spinal cord injury. J. Neurotrauma. 2000, 17: 915-925), the formation of cavities surrounded by an astroglial scar evolving to become multi-lobed cystic cavities functioning as a physical and chemical barrier that prevents axonal regeneration (Houle J D, Tessler A. Repair of chronic spinal cord injury. Exp Neurol. 2003; 182: 247-260; Profyris C, Cheema S S, Zang D, Azari M F, Boyle K, Petratos S. Degenerative and regenerative mechanisms governing spinal cord injury. Neurobiol Dis. 2004; 15: 415-436).

For years, tissue or cell transplants have been done after a SCI to promote axonal growth, the spinal cord regeneration and therefore the functional recovery (Zompa E A, Cain L D, Everhart A W, Moyer M P, Hulsebosch C E. Transplant therapy: recovery of function after spinal cord injury. J. Neurotrauma. 1997; 14: 479-506; Taoka Y, Okajima K. Spinal cord injury in the rat. Prog Neurobiol. 1998; 56: 341-358). Transplants using neural stem cells and multipotential precursor cells of embryo or fetus within the injury site have been performed (Stokes B T, Reier P J. Fetal grafts alter chronic behavioral outcome after contusion damage to the adult rat spinal cord. Exp Neurol. 1992, 116: 1-12, McDonald J W, Liu X Z, Qu Y, Liu S, Mickey S K, Turetsky D, Gottlieb D I, Choi D W. Transplanted embryonic stem cells survive, differentiate and promote recovery in injured rat spinal cord. Nat Med 1999, 5: 1410-1412), transplant of fetal cells or fetal spinal cord tissue (Zompa E A, Cain L D, Everhart A W, Moyer M P, Hulsebosch C E. Transplant therapy: recovery of function after spinal cord injury. J. Neurotrauma. 1997, 14: 479-506, Coumans J V, Lin T T, Dai H N, MacArthur L, McAtee M, Nash C, Bregman B S. Axonal regeneration and functional recovery after complete spinal cord transection in rats by delayed treatment with transplants and neurotrophins. J. Neurosci. 200; 21: 9334-9344) and transplants of peripheral nerve and Schwann cells (Menei P, Montero-Menei C, Whittemore S R, Bunge R P, Bunge M B. Schwann cell genetically modified to secrete human BDNF promote enhanced axonal regrowth across transected adult rat spinal cord. Eur J Neurosci 1998, 10: 607-621). Transplants of oligodendrocytes to promote remyelinization (Jeffery N D, Crang A J, O'Leary M T, Hodge S J, Blakemore W F. Behavioral consequences of oligodendrocyte progenitor cell transplant into experimental demyelinating injury in the rat spinal cord. Eur J Neurosci 1999; 11: 1508-1514), the results have had a negative effect on regeneration because they express axonal growth inhibitory molecules (Tessier-Lavigne M, Goodman C S. Perspectives: neurobiology. Regeneration in the nogo zone. Science 2000 287: 813-814). Furthermore, transplants have been done using immature or non-reactive astrocytes to promote regeneration and increase remyelinization and reduce the formation of glial scar (Franklin R J, Crang A J, Blakemore W F. Transplanted type-1 astrocytes facilitate repair of demyelinating injuries by host oligodendrocytes in adult rat spinal cord. J Neurocytol 1991, 20: 420-430). Cells have been transplanted from microglia (Rabchevsky A G, Weinitzen J M, Coulpier M, Fages C, Tinel M, Junier M P. A role for transforming growth factor alpha as an inducer of astrogliosis. J. Neurosci. 1998, 18: 10541-10552), glial cells of the olfactory bulb to create a permissive environment for regeneration (Keyvan-Fouladi N, Li Y, Raisman G. How do transplanted olfactory ensheathing cells restore function? Brain Res Brain Res Rev. 2002; 40: 325-327) and even stem cells have been used, manipulated or not by genetic engineer to induce the synthesis of specific proteins such as neurotrophins, neurotransmitters, enzymes, extracellular matrix molecules and surface adhesion molecules, without obtaining good results in functional recovery (McDonald J W, Liu X Z, Qu Y, Liu S, Mickey S K, Turetsky D, Gottlieb D I, Choi D W. Transplanted embryonic stem cells survive, differentiate and promote recovery in injured rat spinal cord. Nat Med 1999, 5: 1410-1412; Barami K, Diaz F G. Cellular transplant and spinal cord injury. Neurosurgery. 2000; 47: 691-700).

Despite these therapeutic attempts, most of transplants used in the treatment of SCI have failed, being unable to restore significantly the nerve function loss, leading to the development of new strategies as the use of biomaterials to try to repair the spinal cord. First reports worldwide show the use of carbon filaments implants acting as a bridge for the growth of damaged axons in the spinal cord of rats. Khan et al., (Khan T, Dauzvardis M, Sayers S. Carbon filament implants promote axonal growth across the transected rat spinal cord. Brain Res 1991; 541: 139-145) implanted a carbon filament in rats subjected to a complete section model of the spinal cord and they observed the axonal growth on and between the filaments, concluding that the carbon filaments could serve as a surface to bond favorably the growing axons as well as probably functioning as a mechanical guide.

The use of microspheres with nerve growth factor (NGF) encapsulated in ovalbumin joined to biodegradable polymers located at the site of injury, is a bioengineering technique developed in 1999 by Cao and Shoichet (Cao X, Shoichet M S. Delivering neuroactive molecularles from biodegradable microspheres for application in central nervous system disorders. Biomaterials. 1999, 20: 329-339), to promote axonal regeneration processes. This technology was tested in PC12 cells to determine bioactivity of NGF released. The results showed that NGF remains bioactive up to 91 days.

The biocompatible hydrogel of poly[N-(2-hydripropil) methacrylamide] (PHPMA), with a cell adhesion region of fibronectin Arg-Gly and Asp was synthesised and its rheological structure and dielectric properties were characterized by Woerly et al., (Woerly S, Pinet E, de Robertis L, Van Diep D, Bousmina M. Spinal cord repair with PHPMA hydrogel containing RGD peptides (NeuroGel). Biomaterials. 2001; 22: 1095-1111). This biomaterial was tested in a model of spinal cord injury by hemisection in Sprague-Dawley rats. The hydrogel was inserted within the spinal cord. The results showed that the hydrogel polymer provides a three-dimensional structure and continuity through the damaged area, facilitating the migration and reorganization of the cells. Angiogenesis and axonal growth were also observed within the microstructure and new tissue on it, as well as axonal growth going to the supraspinal area within the segment of spinal cord reconstructed, in addition, the presence of hydrogel decreased necrosis and cavities formation, reason why the authors point out that this polymer could be helpful in the injured spinal cord repair.

The use of polymers as tube-like structures that guide the growing axons and serve as a bridge between the transition zone, was a methodology used by Oudega et al., (Oudega M, Gautier S E, Chapon P, Fragoso M, Bates M L, Parel J M, Bunge M B. Axonal regeneration into Schwann cell grafts within resorbable poly(alpha-hydroxyacid) guidance channels in the adult rat spinal cord. Bio-materials. 2001, 22: 1125-1136). Reabsorbable polymers made of poly(D, L-lactic acid) (PLA50) with a co-polymer of high molecular weight of poly(L-lactic acid) mixed with 10% of oligomers of poly (L-lactic acid) (PLA100/10) were implanted in nervous tissue of Fisher strain adult rats that underwent a complete section of the spinal cord, in this study a 4-month follow-up was carried out. The results showed that since week 2, the tubes had spinal nervous tissue and blood vessels. Most of the myelinated axons were found 1 month after implantation. In this paper it is concluded that there is myelinated fibers growth within the implant made with PLA100/10 polymer, 2 months after being placed within the spinal cord. However, there was an evident decrease of this phenomenon 4 months later, reason why the authors recommend further studies to optimize this technique.

Another biodegradable material manufactured to facilitate the regeneration process and guide the growth of axons after a SCI, are the filaments made with poly-□-hydroxybutyrate (PHB) and fibronectin alginate+hydrogel. In a study conducted by Novikov et al., (Novikov L N, Novikova L N, Mosahebi A, Wiberg M, Terenghi G, Kellerth J O. A novel biodegradable implant for neuronal rescue and regeneration after spinal cord injury. Biomaterials. 2002; 23: 3369-3376), sectioning of the rubrospinal tract at the L1 vertebra level was performed, and it was observed that implantation of PHB reduces cellular death by 50%. The use of separate components has no effect on survival of neurons. Also, neonatal Schwann cells were added to transplant of PHB, observing regeneration of axons within the implant and throughout the nervous tissue, suggesting that the use of these biomaterials, plus Schwann cells, can serve as a neuronal support with an increased regeneration after SCI.

The use of hydrogel tubes made of poly(2-hydroxyethyl methacrylate-co-methyl methacrylate) (p(HEMA-co-MMA)), as potential axonal growth guidance channels in the central nervous system is another approach to restore spinal cord injury. The characteristics of these tubes are: softness and flexibility similar to a gel with interconnected macropores between the layers, controlled through a chemical formulation (Dalton P D, Flynn L, Shoichet M S. Manufacture of poly(2-hydroxyethyl methacrylate-co-methyl methacrylate) hydrogel tubes for use as nerve guidance channels. Biomaterials. 2002, 23: 3843-3851).

However, it has been shown that degradation of these polymers can cause an inflammatory reaction, although some of them are immunologically inert and especially resistant within the nervous system (Marchant R E, Anderson J M, Dillingham E O In vivo biocompatibility studies. VII. Inflammatory response to polyethylene and to a cytotoxic polyvinylchloride. J Biomed Mater Res 1986, 20: 37-50; Gautier S E, Oudega M, Fragoso M, Chapon P, Plant G W, Bunge M B, Parel J M. Poly(alpha-hydroxyacids) for application in the spinal cord: resorbability and biocompatibility with adult rat Schwann cells and spinal cord. J Biomed Mater Res 1998, 42: 642-654). Other authors have reported that for some polymers, adhesion of axons to these compounds is poor, however, Rangappa et al. (Rangappa N, Romero A, Nelson K D, Eberhart R C, Smith G M. Laminin-coated poly(L-lactide) filaments induce robust neurite growth while providing directional orientation. J Biomed Mater Res 2000, 51: 625-634), using nets coated with a matrix of laminin, were able to increase adhesion of axons to the matrix. Another strategy is the development of biomaterials with the capacity to bind encapsulated peptides (trophic factors, drugs, etc.), which are slowly released (Pechar M, Ulbrich K, Subr V, Seymour L W, Schacht E H. Poly(ethylene glycol) multiblock copolymer as a carrier of anti-cancer drug doxorubicin. Bioconjug Chem 2000, 11: 131-139) but not satisfactory results have been obtained. Collagen fibers alone or in combination with other materials have served as guide and support for axonal growth and for inducing regeneration (Heffner C D, Lumsden A G, O'Leary D D. Target control of collateral extension and directional axon growth in the mammalian brain. Science. 1990; 247: 217-220; Tong X J, Hirai K, Shimada H, Mizutani Y, Izumi T, Toda N, Yu P. Sciatic nerve regeneration navigated by laminin-fibronectin double coated biodegradable collagen grafts in rats. Brain Res 1994, 663: 155-162). The use of biocompatible materials to restore the damaged nervous tissue has advanced rapidly, developing materials that function as bridges to repair spinal cord, however, these polymers are synthesised traditionally by chemical methods or electrochemical polymerization (Wang J, Neoh K G, Kang E T. Comparative study of chemically synthesised and plasma polymerized pyrrole and thiophene thin films. Thin Solid Films 2004, 446: 205-217), which could interfere with their beneficial effects, since it has been shown that degradation of these polymers can cause an inflammatory reaction.

Biodegradable polymers synthesised from the mixture and combination of segments of pyrrole and thiophene with flexible aliphatic ester chains to facilitate their degradation, were described by Schmidt et al. (U.S. Pat. No. 6,696,575 B2, 2004), these ones have been proposed as an alternative treatment in the field of tissue engineering, given their chemical and electrical properties. These materials are flexible and its chemical structure allows free movement of electrons between the chains, increasing their conductive properties. In this patent, they are suggested as biomaterials to promote regeneration of peripheral nervous tissue of the spinal cord, as well as in other tissues (bone, muscle, etc.). However, evidences are not presented to support its use.

The use of plasma to obtain conductive polymer films is another methodology that has been used for the synthesis of polymers. During the synthesis process, monomers react in the gaseous phase of the procedure and do not need a chemical intermediary in the reaction. With this method, the chemical structure of polymers is different from that observed with chemical synthesis, showing higher purity, greater adherence and increased crossings and extensions (Wang J, Neoh K G, Kang E T. Comparative study of chemically synthesised and plasma polymerized pyrrole and thiophene thin films. Thin Solid Films 2004, 446: 205-217). Cruz et al (Cruz G J, Morales J, Olayo R. Films obtained by plasma polymerization of pyrrole. Thin Solid Films 1999, 342: 119-126) reported the plasma synthesis method of pyrrole-derived materials, among which those iodine-doped are found. These materials are not biodegradable, reason why their use in the nervous system would reduce inflammatory response conferring them higher efficiency, since several studies indicate that the inflammatory response is one of the mechanisms of secondary damage that destroy nerve tissue located in the periphery of the injury.

The conductive polymers are those materials formed by long chains of hydrocarbons with double bonds alternated or conjugated; which meet the electrical properties of metals and the mechanical properties of plastics. Its conductivity is mainly due to the addition of certain amounts of other chemicals products (doping), but also to the presence of conjugated double bonds that allow the passage of an electron flow. The doping technique involves the addition of atoms having electronegative properties. These atoms can act providing free electrons to polymeric bonds or subtracting electrons, which equals to generate positive charges. In both cases, the polymer chain becomes electrically unstable and if a potential difference is applied, electrons move through the polymer (Cruz G J, Morales J, Olayo R. Films Obtained by plasma polymerization of pyrrole. Thin solid films 1999, 342: 119-126). Although the physical mechanisms that change polymers toward conductors are not well known, the purity and organization of the polymer chains seem to have a great importance. Thus, when the structural organization of polymer is modified, the conductivity can be improved. The polymers used as conductors are composed mainly of carbon and hydrogen atoms, arranged in repeated monomer units, like any other polymer. In general, these units usually have a heteroatom as nitrogen or sulfur. The C atoms are linked together by an alternative set of single and double bonds ( . . . =C—C=C—C=C— . . . ), i.e., they show hyperconjugation of bonds, this is a general characteristic of all conductive polymers. The conduction of electricity is due to the motion of electrons (e−). It is necessary for e− to move freely through the material. In solid conductors, e− move through discrete energy states called bands (originated from the extension of Molecular Orbital Theory to the entire solid-crystalline network). Solids can conduct electricity only if their last band is half full (good conductor or metallic conductor) or, if empty, it is found energetically near the last full band (semiconductor). If the jump filled-band→empty-band is energetically big this can be considered as an insulator (Cruz G J, Morales J, Olayo R. Films Obtained by plasma polymerization of pyrrole. Thin solid films 1999, 342: 119-126).

The polypyrrole (PPy) is a conductive polymer with a chemical structure positively charged to which various chemicals substances (dopants) can join to change its electrical properties. The PPy has been used as a biosensor (Lopez-Crapez E, Livache T, Marchand J, Grenier J. K-ras mutation detection by hybridization to a polypyrrole DNA chip. Clin Chem 2001; 47: 186-194), to detect glucose in blood, because of its biocompatibility. Furthermore, because of its conductive properties, it has been shown that PP has the capacity to stimulate proliferation of nerve cells (Kotwal A, Schmidt C E. Electrical stimulation alters protein adsorption and nerve cell interactions with electrically conducting biomaterials. Biomaterials. 2001; 22: 1055-1064), chromaffin cells (Aoki T, Tanino M, Sanui K, Ogata N, Kumakura K. Secretory function of adrenal chromaffin cells cultured on polypyrrole films. Biomaterials. 1996; 17: 1971-1974) and endothelial cells (Garner B, Georgevich A, Hodgson A J, Liu L, Wallace G G. Polypyrrole-heparin composites as stimulus-responsive substrates for endothelial cell growth. J Biomed Mater Res 1999, 44: 121-129). Schmidt et al., (Schmidt C E, Shastri V R, Vacanti J P, Langer R. Stimulation of neurite outgrowth using an electrically conducting polymer. Proc Natl Acad Sci U.S.A. 1997; 94: 8948-8953) showed that electrical stimulation increases neurite growth in PC-12 cells on PP films. Recent studies have demonstrated an acceptable biocompatibility of PP both in vitro (Zhang Z, Roy R, Dugre F J, Tessier D, Dao L H. In vitro biocompatibility study of electrically conductive polypyrrole-coated polyester fabrics. J Biomed Mater Res 2001, 57: 63-71) and in vivo (Jiang X, Marois Y, Traore A, Tessier D, Dao L H, Guidoin R, Zhang Z. Tissue reaction to polypyrrole-coated polyester fabrics: an in vivo study in rats. Tissue Eng. 2002; 8: 635-647), this background gives support for using the PPy and its derivatives in several biomedical and tissue engineering applications. Based on this information, it was decided to use two semiconductive polymers, the polypyrrole co-polymer with polyethylene glycol (PPy/PEG) and a polymer of iodine-doped polypyrrole (PPy/I) in a model of complete section of rat spinal cord.

SUMMARY OF THE INVENTION

Synthesis of Polypyrrole/Polyethylene Glycol Copolymer and Iodine-Doped Polypyrrole Polymers were synthesised in a thin film form by means of electric glow discharges in a glass tubular reactor of 9 cm in diameter and 30 cm long with stainless steel flanges. The pressure is $1.5 \times 10^{-2}$ Torr to initiate polymerization and $5 \times 10^{-2}$ Torr for the propagation of polymerization. The electric field oscillation frequency was 13.5 MHz. Stainless steel electrodes are 7 cm in diameter. One of the electrodes was connected to ground and the other was connected to RF signal, the separation between them was 9 cm. The monomer and the dopant were placed in separate containers, and a small vapor flow of them was introduced to the reactor due to the pressure difference between the reactor and the vessels, both were mixed within the reactor. The temperature of the reactants was approximately 20° C. The polymerization time was 300 min. The reactions primarily occur in the gas phase and end in the solid phase when the molecular weight of the polymer increases. The condensed formula of starting reagent is: $C_4H_5N$.

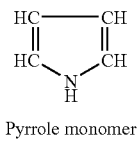

Pyrrole monomer

Polymers were separated from the surface of the reactor after being subjected to several cycles of wetting with acetone and drying. After 2 or 3 cycles, polymers were mechanically recovered with a spatula, later they were ground to make tablets that were used as implants in spinal cord of test subjects. Tablets were prepared from derivatives of iodine-doped polypyrrole (PPy/I) and polypyrrole and polethylene-glycol copolymers (PPy/PEG) for comparison.

Physicochemical Characterization of Plasma-Synthesised Polymers.

Analysis of the Structure by Infrared Spectroscopy

Spectrum of FIG. 1A shows 3 complex absorption bands corresponding to PPy/PEG copolymer. The first is between 400 and 1200 $cm^{-1}$, the second between 1200 and 2000 $cm^{-1}$ and the third between 2400 and 3600 $cm^{-1}$. The broad peak covering the range between 400 and 1200 $cm^{-1}$ contains many absortions corresponding to alkenes. The peak width indicates branching, crosslinking and the interaction between PPy rings. The most intense peaks correspond to the vibrations of PPy.

FIG. 1B shows the transmittance spectrum of the PPy/I sample, 2 complex wide bands of vibration are seen, characteristic of plasma-synthesised polymers. The first between 2400 and 3600 $cm^{-1}$ and the other between 500 and 1800 $cm^{-1}$. The area between 3600 and 2400 $cm^{-1}$ shows absorption of bonds N—H, O—H and C—H in different configurations, highlighting the vibration of primary amines (C—N) in 3349 $cm^{-1}$, as well as the saturation of aliphatic chains located in 2932 $cm^{-1}$. In the second complex band, the vibrations corresponding to primary, secondary and tertiary amines in 1639 $cm^{-1}$ are highlighted. The deformation of the methyl (C—H) is in 1452 $cm^{-1}$. In 747 $cm^{-1}$, the vibrations corresponding to C—C bonds are shown.

Electrical Characteristics

The PPy/PEG showed a resistance of G$\Omega\square$, being considered as a semiconductor polymer. The PPy/I showed a resistance of 1.3 M$\Omega$, with a resistivity of 45.94 M$\Omega$-cm and an aproximated conductivity of 21 nS/cm.

Morphology

In FIG. 2A it is shown an image of the surface of PPy/PEG copolymer taken by scanning electronic microscopy, in which a homogeneous structure is observed whose surface is of spongy appearance. In FIG. 2B it is shown the image corresponding to the PPy/I polymer, at the surface small clumps of material with a size of approximately 5 to 10 $\square$m can be seen.

PPy/PEG copolymer was microscopically obtained in thin films while PPy/I polymer was pulverized and subsequently compacted to form a tablet.

PREFERRED MODE OF CARRYING OUT THE INVENTION

Figure 1A:
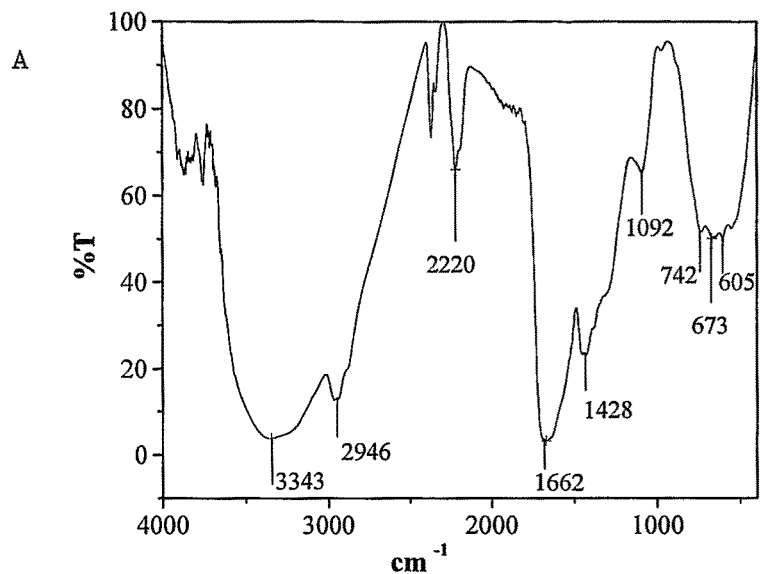
FIG. 1. (A) FT-IR spectrum of polypyrrole/polyethylene glycol copolymer; (B) FT-IR spectrum of the iodine-doped polypyrrole polymer.
Figure 1B:
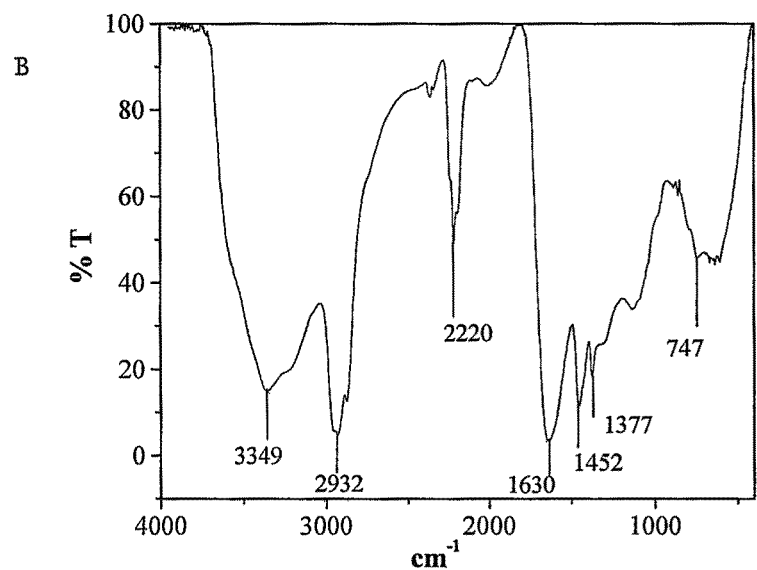
Figure 2A:
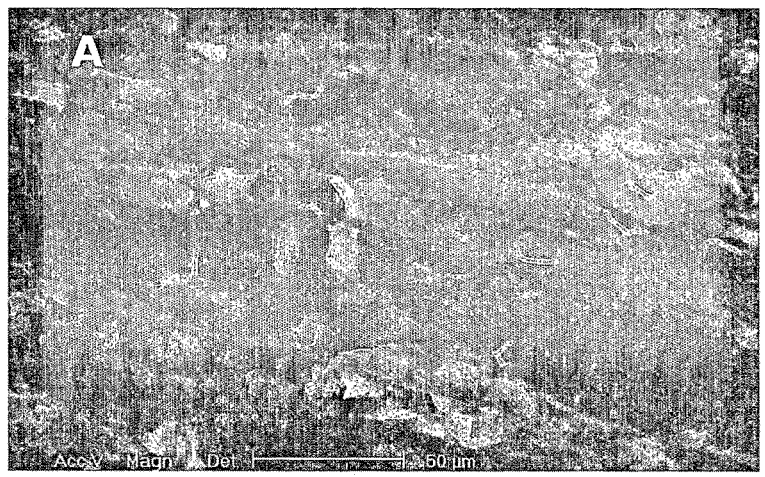
FIG. 2. Photomicrographs taken with scanning electronic microscopy of implanted biomaterials. (A) Polypyrrole copolymer with polyethylene glycol. (B) Iodine-doped polypyrrole. The bar corresponds to 50 μm.
Figure 2B:
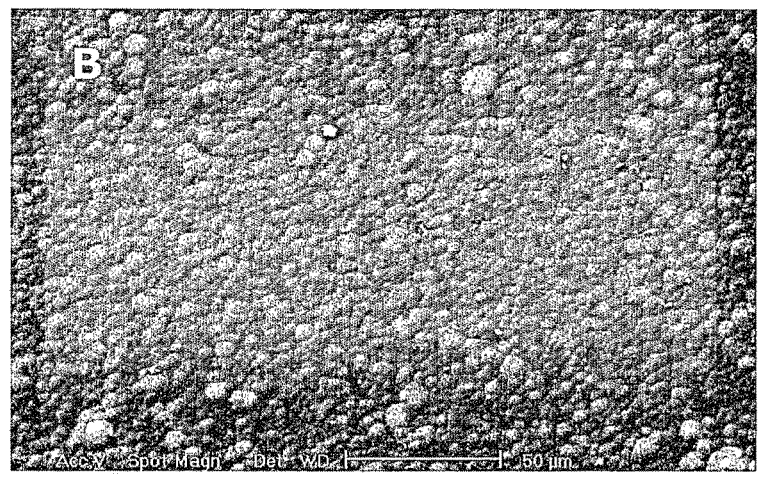

Assessment of the Neuronal Reconnection Effect of Plasma-Synthesised Pyrrole-Derived Polymers Plasma-synthesised polymers were evaluated as neuroprotectors and neuroregenerators of nerve function in the complete section model of spinal cord in rats.

Three experimental groups were formed with three animals each, as follows: A) Control Group. Animals with complete section of spinal cord at 9th thoracic vertebra level (T9), B) PPy/PEG Group. Animals with complete section of spinal cord and with implant of PPy/PEG, C) PPy/I Group, animals that underwent the surgical procedure described above and PPy/I tablets were implanted. All experimental groups were formed with 3 rats each.

The animals were anesthetized by intramuscular with a mixture of 77.5 mg ketamine and 12.5 mg xylazine hydrochloride per kg of body weight. After anesthetizing the animal and cleaning on surgical site, a sagittal incision was done in the skin, followed by disection of para-vertebral muscles of the spinal apophysis.

Two spinal apophysis were removed from T9-T10 to observe the laminar processes of these vertebrae. Finally, a 2-level laminectomy was conducted, extending it bilaterally to facetary processes. The meninges remained intact. Upon completion of laminectomy, a longitudinal incision was performed in the meninges of about 5 mm long, referring both sides of incision with a single point of suture of 9-0 (polyamide 6 monofilament) subsequently it was made a complete cross section of spinal cord, and was corroborated by a microsurgical hook that no nerve pathway was still connected.

Immediately after completing the injury process by complete section of the spinal cord in rats, right in the site section it was transversally introduced a piece of polymer tablet of approximately 3 mm in diameter. After implantation, a 9-0 suture was made through the meninges with simple suture points. Finally, surgical incision was sutured in 2 planes, the muscular fascia and skin with simple and continuous points, respectively, with 5-0 suture (polypropylene monofilament).

After surgery, the animals were under observation at room temperature in a single cage, with a diet of commercial food and water, on free demand, mixed with paracetamol concentration 3.2 g/100 mL (10 mL diluted to 2 l water, administered in the drinking water for 72 hrs), also 250 μL/250 g of weight of benzathine penicillin were intramuscularly administered (1,200,000 I.U. as single dose).

Evaluation of the Polymers Regenerative Effect

To determine the inductor effect of regeneration of biomaterials, motor function recovery was evaluated in animals for 4 weeks after the section of the spinal cord, using BBB scale (Basso, Bettie and Bresnahan) (Basso D M, Beattie M S, Bresnahan J C. Graded histological and locomotor outcomes after spinal cord contusion using the NYU weight-drop device versus transection. Exp Neurol. 1996; 139: 244-256), as described below:

BBB scale
Grade 0
Major movements in the hind limbs (EP) are not observed.
Grade 1
Limited movement (arc<50%) of one or two joints, usually the hip and/or knee.
Grade 2
Wide movement (arc>50%) of a joint with or without limited movement of the other.
Grade 3
Wide movement of two joints.
Grade 4
Limited movement of the three joints of EP (hip, knee and ankle).
Grade 5
Limited movement of two joints and wide of the third one.
Grade 6
Wide movement of two joints and limited of the third one.
Grade 7
Wide movement of the three joints of EP (hip, knee and ankle).
Grade 8
Rhythmic movements (coordinated) of both EP legs without weight support or plantar placement but without supporting the weight.
Grade 9
Plantar placement with weight support when not walking or occasional steps (<0=50%), frequent (51% to 94%) or constant (95% to 100%) with dorsal weight support, without plantar support.
Grade 10
Occasional steps with plantar weight support, without coordination between fore limbs (EA) and EP.
Grade 11
Frequent or constant steps with plantar weight support, without coordination between EA and EP.
Grade 12
Frequent or constant steps with plantar weight support and occasional coordination between EA and EP.
Grade 13
Frequent or constant steps with plantar weight support and frequent coordination between EA and EP.
Grade 14
Constantly taking steps with plantar weight support, constant coordination between ES and EI, and there is internal or external rotation of legs, mainly when making contact with the floor or when taking off. Also frequent plantar steps, constant coordination between EA and EP and occasional dorsal steps.
Grade 15
Constant plantar and coordinated steps between EA and EP. It does not separate the toes or only occasionally when it advances the leg forward. When making contact with the floor, parallel alignment of the leg to the body predominates.
Grade 16
Plantar and coordinated steps between EA and EP, constant during the march. The separation of the toes often occurs when the leg advances forward. When making contact with the floor, parallel alignment of the leg to the body predominates, but it rotates it as it lifts the leg.
Grade 17
Plantar and coordinated steps between EA and EP, constant during the march. The separation of the toes often occurs when it advances the leg forward. When making contact with the floor, parallel alignment of the leg to the body predominates, but as it lifts the leg, it keeps it aligned (without rotation).
Grade 18
The separation of the toes is constant during the march. When making contact with the floor, parallel alignment of the leg to the body predominates, but it rotates it as it lifts the leg.
Grade 19
Plantar and coordinated steps between EA and EP, constant during the march. The separation of the toes constantly occurs during the march. When making contact with the floor and lifting it, parallel alignment of the leg to the body predominates. Drags the tail part of or all the time.
Grade 20
Plantar steps, coordinated walk and constant separation of the toes. When making contact with the floor and lifting it, parallel alignment of the leg to the body predominates, the tail constantly raised and trunk instability.
Grade 21
Similar but constantly stable trunk.

Evaluation of the Polymers Neuroprotective Effect

The neuroprotective effect and the polymers integration could be seen in histologic sections one month after the injury. The animals were perfused by intracardiac route. Following perfusion, spinal cord was removed in order to obtain a segment of 1.5 cm from the epicenter injury region to the caudal segment and to the cephalic segment of the spine. Tissue was placed in fixative for 5 days, after which followed the procedure so as to be embedded in paraffin. 10 µm-thick sequential longitudinal cuts were made in a microtome, selecting the cuts in a range of 10 sections obtaining 4 samples. The selected cuts were passed to a flotation water bath at 45° C., they were placed on glass plates to be stained with the Harris' procedure of hematoxylin and eosin.

Statistical Analysis

The results were analyzed using parametric statistics when showing a normal distribution and homogeneity of variances. ANOVA test with repeated measures was used followed by Dunnett's test.

Values were taken at $p<0.05$ to determine the limit of statistical significance.

Results

Figure 3:
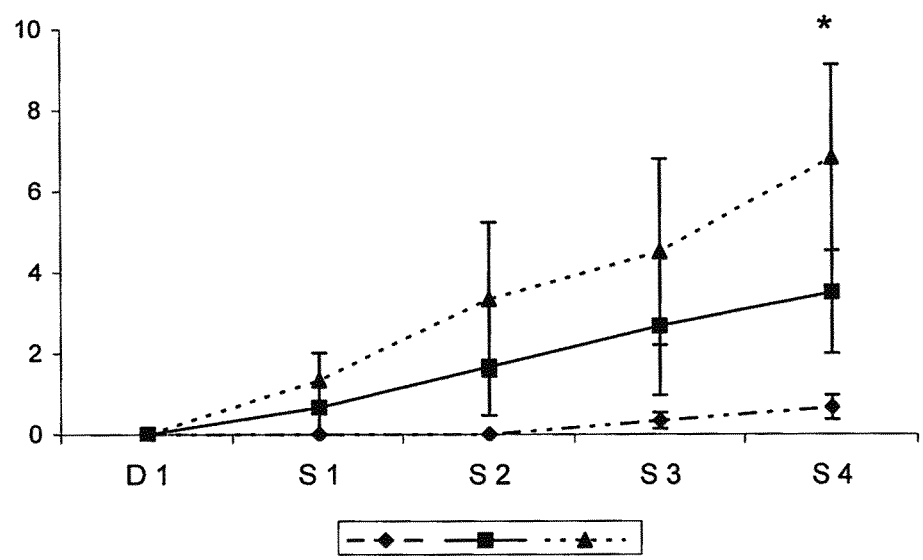
FIG. 3. Graphic that shows the motor recovery results assessed with the BBB scale (Basso, Beattie and Bresnahan) from the first day of injury (D1) and for 4 weeks (S) after the complete section of spinal cord.

The results of the functional assessment are shown in FIG. 3. In this study recovery was observed 5 times greater in animals implanted with PPy/PEG with regard to the control group, also, the recovery of the PPy/l group was 10 times higher compared with the control group ($p<0.05$). In both groups receiving implants, the functional recovery indicates that animals have voluntary nerve function, since grade 4 using the BBB scale observed in animals with PPy/PEG evaluates the presence of limited movement of the three joints of the hind limbs (hip, knee and ankle), while the average grade 7 reached by animals with PPy/l indicates the development of wide movements of the three joints of the hind limbs (hip, knee and ankle). Abbreviations in the graphic correspond to: Section: complete spinal cord section without transplant, Section+PP/PEG: Complete spinal cord section plus transplant of polypyrrole and polyethylene glycol co-polymer, complete spinal cord section plus transplant of iodine-doped polypyrrole. The results are expressed as mean±SE of 3 animals per group. The results were analyzed with an ANOVA of repeated measures followed by Dunnett's test. * $p<0.05$.

Figure 4:
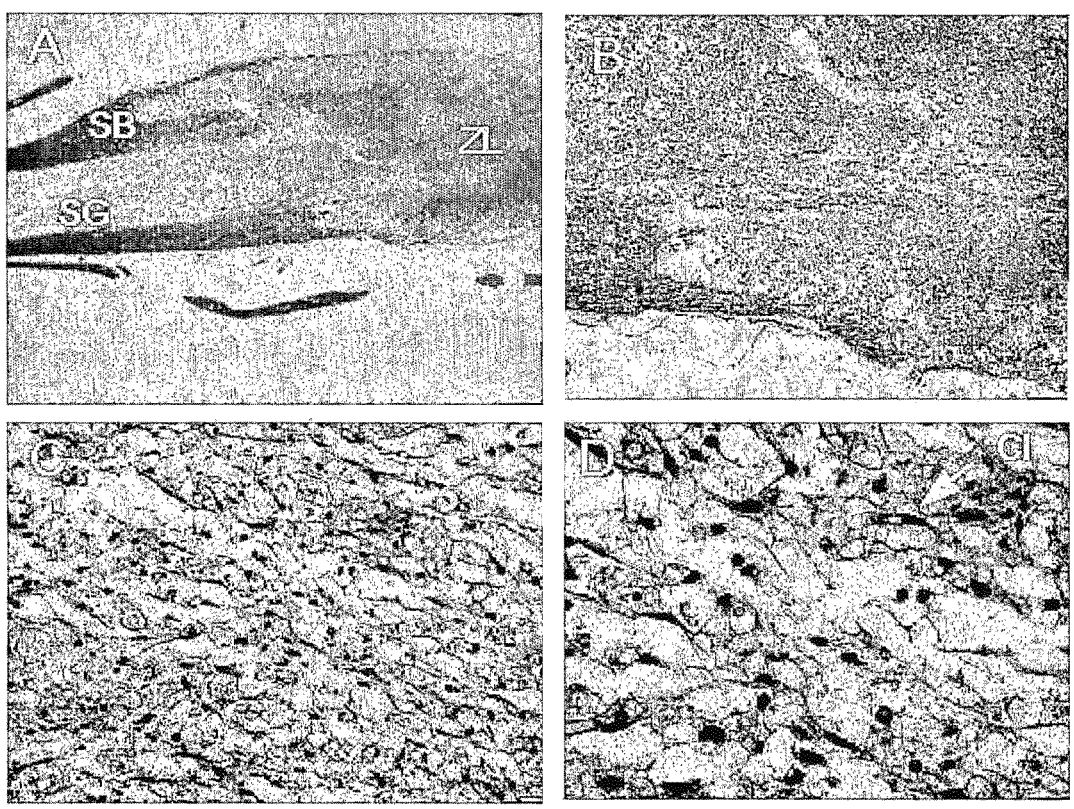
FIG. 4. Longitudinal sections of spinal cord in an animal with complete section of spinal cord and without implant one month after the injury. (A) Injury zone and preserved tissue (2.5×); (B) Detail of transition zone (5×); (C) Loss of cytoarchitecture in the injury zone (20×); (D) Presence of inflammatory cells (40×). Hematoxylin/eosin technique. SB: White substance, SG: Gray substance, ZL: Injury zone, CI: Inflammatory cells.
Figure 5:
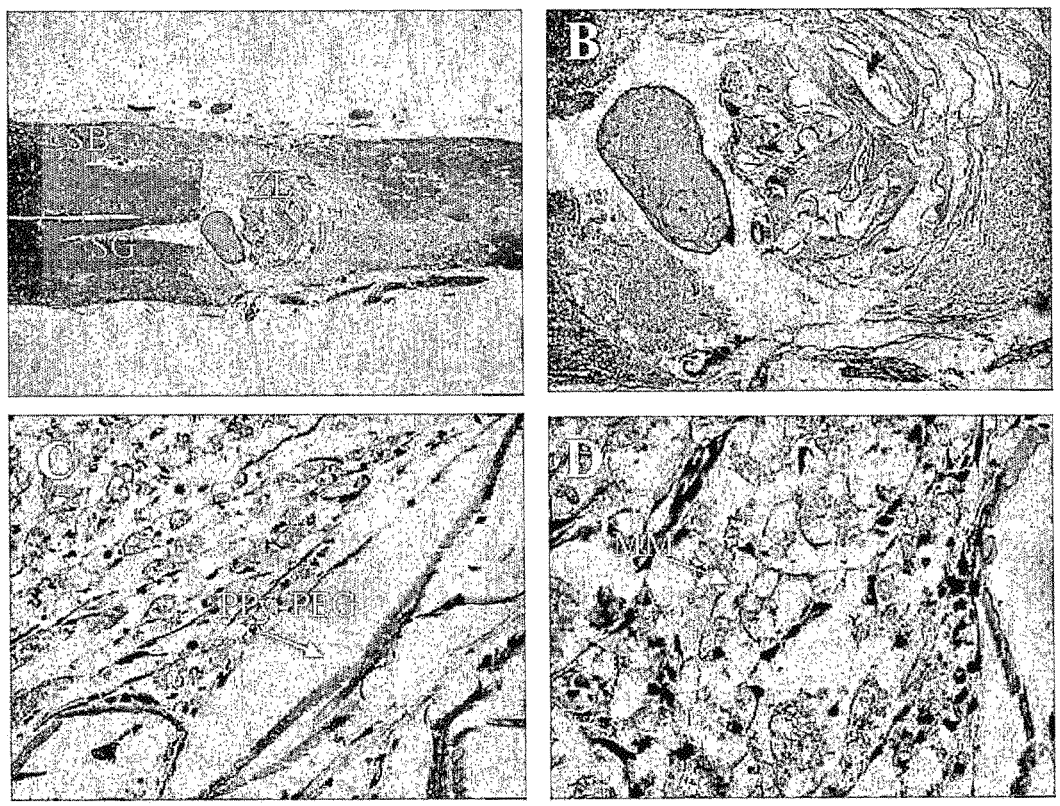
FIG. 5. Longitudinal sections of spinal cord of an animal with complete section of spinal cord and with an implant of polypyrrole/polyethylene glycol copolymer one month after the injury. (A) Image that shows the implant integration to nerve tissue (2.5×); (B) Detail of transition zone (5×); (C) injury zone (20×); (D) Presence of inflammatory cells (40×). SB: White substance, SG: Gray substance, ZL: Injury zone, CI: Inflammatory cells. Hematoxylin/eosin technique. SB: White substance, SG: Gray substance, ZL: Injury zone, PPy/PEG: Transplant of polypyrrole and polyethylene glycol copolymer, MM: Modified macrophages.
Figure 6:
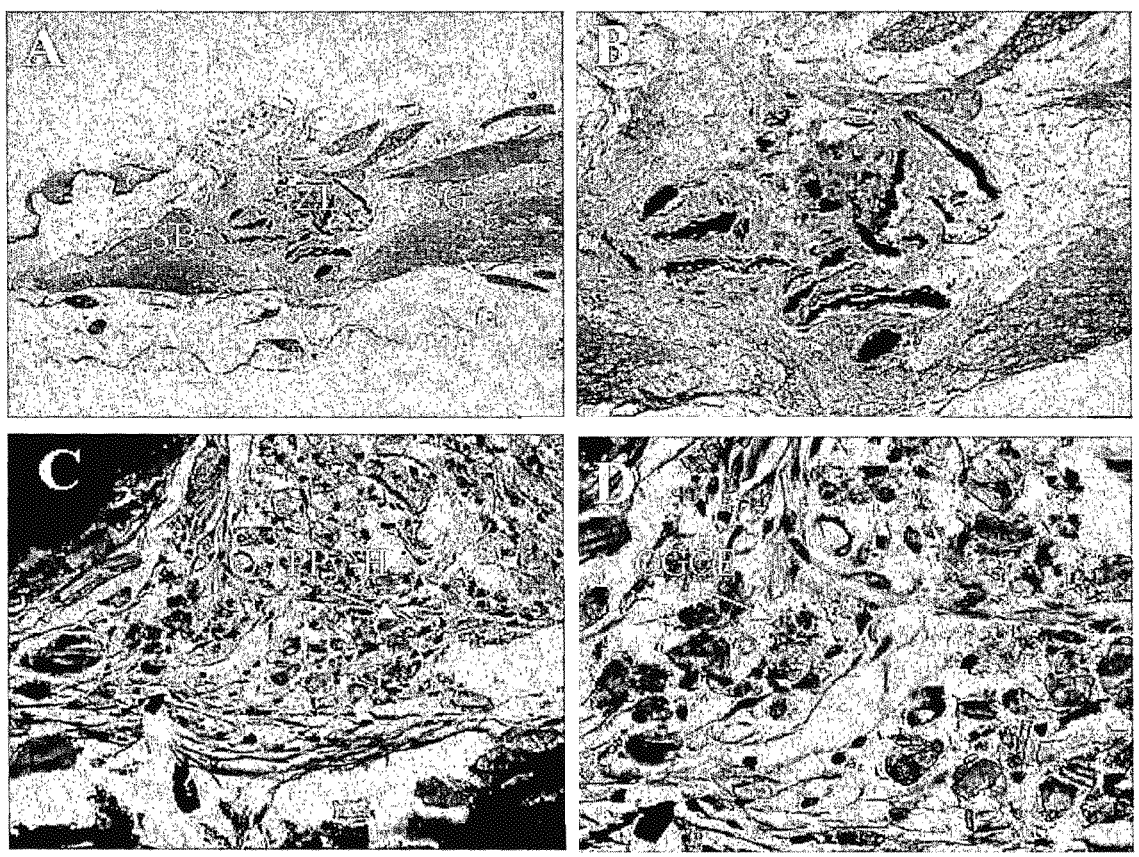
FIG. 6. Longitudinal sections of spinal cord of an animal with complete section of spinal cord and implant of halogen-doped polypyrrole, one month after injury. (A) Image that shows the implant integration to nerve tissue (2.5×); (B) Detail of transition zone (5×); (C) Injury zone (20×); (D) Presence of inflammatory cells (40×). SB: White substance, SG: Gray substance, ZL: Injury zone, CI: Inflammatory cells. Hematoxylin/eosin technique. SB: White substance, SG: Gray substance, ZL: Injury zone, PPy/I. Transplant of iodine-doped polypyrrole, CGCE: foreign body giant cells.

The results of the histological study are shown in FIGS. 4, 5 and 6. In control group, extensive destruction of nerve tissue and an increased presence of inflammatory cells were observed. In PPy/PEG Group a lower destruction of nerve tissue was observed, there were no foreign body giant cells, however, spongy macrophages, inflammatory cells and T lymphocytes are present. In PPy/l Group the implanted polymer joined the nervous tissue of the spinal cord, inflammatory cells were also observed, T lymphocytes and macrophages modified called foreign body giant cells. The abbreviations shown in the images indicate: FIG. 4, (A) Injury zone and preserved tissue (2.5×); (B) Detail of transition zone (5×); (C) Loss of cytoarchitecture in the injury zone (20×); (D) Presence of inflammatory cells (40×). SB: White substance, SG: Gray substance, ZL: Injury zone, CI: Inflammatory cells. FIG. 5 (A) Image where the implant integration to nerve tissue (2.5×) can be observed; (B) Detail of transition zone (5×); (C) Injury zone (20×); (D) Presence of inflammatory cells (40×). SB: White substance, SG: Gray substance, ZL: Injury zone, CI: Inflammatory cells. Hematoxylin/eosin technique. SB: White substance, SG: Gray substance, ZL: Injury zone, PPy/PEG: Transplant of polypyrrole and polyethylene glycol copolymer, MM: Modified macrophages. FIG. 6, (A) Image in which implant integration to nerve tissue can be observed (2.5×); (B) Detail of transition zone (5×); (C) Injury zone (20×); (D) Presence of inflammatory cells (40×). SB: White substance, SG: Gray substance, ZL: Injury zone, CI: Inflammatory cells. Hematoxylin/eosin technique. SB: White substance, SG: Gray substance, ZL: Injury zone, PPy/l. Transplant of iodine-doped polypyrrole, CGCE: Foreign body giant cells.

Figure 7:
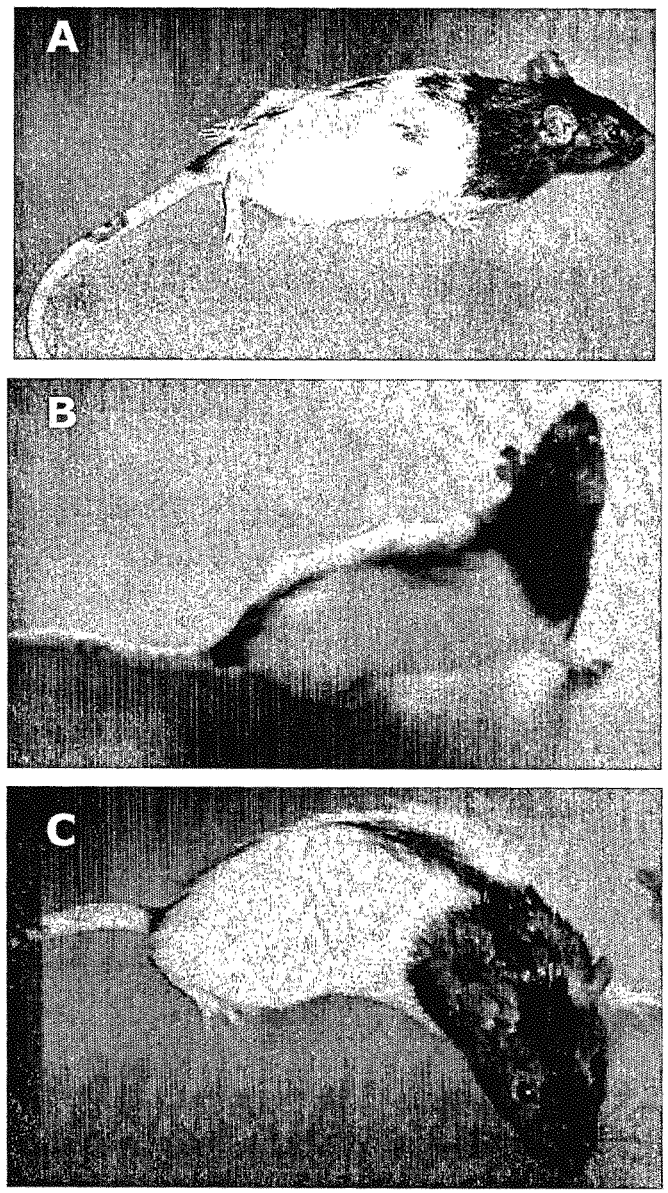
FIG. 7. Images representing the overall health and functional recovery of animals at the end of the study. (A), Animal control without implant; (B) Animal with implant of polypyrrole/polyethylene glycol copolymer and (C), Animal with implant of polypyrrole/iodine.

The results of the weekly observations of the overall health conditions of animals are shown in FIG. 7. In these images, it can be observed the absence of skin infections. Likewise, in the exploratory analysis it was confirmed that during monitoring, no respiratory and kidney infections were observed. Finally, this study found no adverse effects or biomaterials rejection with a survival of 100%. Panels shown in the figure correspond to: (A), Control animal without implant, (B) Animal with implant of polypyrrole/polyethylene glycol copolymer and (C), Animal with implant of polypyrrole/iodine.

Results indicate that the plasma-synthesised polymers are effective as neuro-protectors and neuro-regenerators of the spinal cord after an injury due to a complete section in the rat, without serious side effects.

The invention claimed is:

1. An implant comprising a polypyrrole and polyethylene glycol copolymer obtained by a plasma-synthesis method, said implant promoting, when implanted in a suitable host, neuroprotection and reconnection of the spinal cord after an injury.

2. The implant of claim 1, wherein said plasma-synthesis method comprises the steps of:
   a) polymerizing monomers of pyrrole and ethylene glycol by mixing a vapor flow of them in a reactor and applying electric glow discharges, the polymerization being carried out at a pressure of $1.5 \times 10^{-2}$ Torr to initiate polymerization and at a pressure of $5 \times 10^{-2}$ Torr for the propagation of polymerization; an electric field oscillation frequency of 13.5 MHz; a temperature of the reactants of approximately 20° C.; and a polymerization time of 300 minutes;
   b) separating the copolymers obtained by subjecting them to 2 or 3 cycles of wetting with acetone;
   c) drying the copolymers; and,
   d) mechanically recovering the copolymers obtained.

3. An implant according to claim 1, wherein the implant is capable of improving tissue integration and reducing inflammatory reaction in the spinal cord when administered to a patient in need thereof.

* * * * *